United States Patent
Kang et al.

(10) Patent No.: US 10,857,206 B2
(45) Date of Patent: Dec. 8, 2020

(54) COMPOSITION FOR REGULATING CUTANEOUS PIGMENTATION OR SKIN WHITENING COMPRISING SDF1

(71) Applicant: AJOU UNIVERSITY INDUSTRY-ACADEMIC COOPERATION FOUNDATION, Suwon-si (KR)

(72) Inventors: Hee Young Kang, Yongin-si (KR); Tae Jun Park, Seoul (KR); Jung Eun Yoon, Suwon-si (KR); Mi Sun Kim, Suwon-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 16/174,293

(22) Filed: Oct. 30, 2018

(65) Prior Publication Data

US 2019/0125835 A1 May 2, 2019

(30) Foreign Application Priority Data

Oct. 30, 2017 (KR) .................. 10-2017-0142285

(51) Int. Cl.
| | |
|---|---|
| *A61K 38/18* | (2006.01) |
| *A61Q 19/02* | (2006.01) |
| *C12N 15/62* | (2006.01) |
| *A61P 17/00* | (2006.01) |

(52) U.S. Cl.
CPC .............. *A61K 38/18* (2013.01); *A61P 17/00* (2018.01); *A61Q 19/02* (2013.01); *C12N 15/62* (2013.01)

(58) Field of Classification Search
CPC .......... A61K 38/18; A61K 8/64; A61Q 19/02; C12N 15/62; A61P 17/00
See application file for complete search history.

(56) References Cited

U.S. PATENT DOCUMENTS

| | | | | |
|---|---|---|---|---|
| 7,405,195 | B2 * | 7/2008 | Chen | ............... A61Q 19/00 514/18.8 |
| 2009/0285785 | A1 * | 11/2009 | Jimi | ............... A61K 38/193 424/93.7 |
| 2017/0273909 | A1 * | 9/2017 | Mathiowitz | ............ A61K 38/28 |

FOREIGN PATENT DOCUMENTS

JP       2015229654 A   * 12/2015

OTHER PUBLICATIONS

Wachsmuth, R.C. et al. "The Effect of Sun Exposure in Determining Nevus Density in UK Adolescent Twins" J. Invest. Derm. 2005, 124 (1), 56-62 (Year: 2005).*
Nevus.com (https://www.nevus.org/what-is-a-large-cmn) 2018, pp. 1-3 (Year: 2018).*
Guo, R. et al. "Stromal cell-derived factor 1 (SDF-1) accelerated skin wound healing by promoting the migration and proliferation of epidermal stem cells" In Vitro Cell. Dev. Biol.—Animal 2015, 51, 578-585 (Year: 2015).*
Machine translation of JP-2015229654-A, 2019, pp. 1-7 (Year: 2019).*
Rui Guo et al., "Stromal cell-derived factor 1 (SDF-1) accelerated skin wound healing by promoting the migration and proliferation of epidermal stem cells", In Vitro Cell.Dev.Biol.—Animal (2015) 51:578-585.

* cited by examiner

*Primary Examiner* — Andrew S Rosenthal
(74) *Attorney, Agent, or Firm* — Revolution IP, PLLC

(57) ABSTRACT

A method of preventing or treating cutaneous pigmentation disease in a subject in need thereof, includes: providing a pharmaceutical composition comprising SDF1, an inducer or activator of SDF1, as an active ingredient; and administering the pharmaceutical composition to the subject, wherein the cutaneous pigmentation is prevented or treated, and the cutaneous pigmentation disease is selected from the group consisting of melasma, freckles, lentigo, nevus, pigmentation by drugs, pigmentation after inflammation and hyperpigmentation incurred from dermatitis.

2 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 350
<212> TYPE: DNA
<213> ORGANISM: Homo sapiens

<400> SEQUENCE: 1
```

-continued

```
gtgggcctgt gattagctca tttcaccatt gagaggtcgg aagtacaaag gctacattcg      60
cttttactga gagccgccgg cgccttctgc tttgtttgta caggcgagga aactgaggct     120
cggctggtgg cgccgtgggc ttggagtccg agccacgctg actgcaaaga cgggtctcat     180
tcccgcagat cgagctctgc cggcggctgc gccgcaagcc gggcaggtgg cgagcttgag     240
cccccacgca cagaaagcag gacccctcg gctgccttgg gccgccaccg ccagcaggcc      300
ctccgcccgg gactaacttg tttgcttttc attggttctc attcagttcc                350
```

COMPOSITION FOR REGULATING CUTANEOUS PIGMENTATION OR SKIN WHITENING COMPRISING SDF1

CROSS-REFERENCE TO RELATED APPLICATION

This application claims priority to and the benefit of Korean Patent Application No. 10-2017-0142285 filed in the Korean Intellectual Property Office on Oct. 30, 2017, the entire contents of which are incorporated herein by reference.

BACKGROUND OF THE DISCLOSURE

1. Field of the Disclosure

The present invention relates to a composition for regulating cutaneous pigmentation or a composition for skin whitening comprising a stromal cell-derived factor 1 (SDF1) as an active ingredient.

2. Description of the Related Art

Epidermal melanocytes synthesize melanin pigments. The crucial role of cutaneous pigmentation is to absorb ultraviolet radiation (UV radiation), which functions as a natural sunscreen. However, excessive production of melanin causes hyperpigmentation, which leads to melasma or solar lentigo. Cutaneous pigmentation by ultraviolet is regulated by interactions between adjacent cutaneous cells such as melanocytes, keratinocytes, fibroblasts or inflammatory cells. Recently, it has been emphasized that in the regulation of pigmentation the above-mentioned interaction contributes to the dermis component. For example, in determining the natural skin color of a human through the secretion of soluble factors such as Dickkopf-related protein-1 (DKK1) and neuregulin-1, dermal fibroblasts have been confirmed to regulate the functions. Melasma or solar lentigo is commonly caused by hyperpigmentary disorders of the face, but its pathogenesis is not well known. Accordingly, interest in factors related to cutaneous pigmentation regulation is increasing.

SUMMARY OF THE DISCLOSURE

It is an object of the present invention to provide a reagent composition for inhibiting in vitro cutaneous pigmentation, a pharmaceutical composition for preventing or treating cutaneous pigmentation disease, a cosmetic composition for skin whitening and a functional health food composition for skin whitening, which comprise stromal cell-derived factor 1 (SDF1), an inducer or activator of SDF1, as an active ingredient, respectively.

It is also another object of the present invention to provide a biomarker composition for diagnosing cutaneous pigmentation disease comprising a SDF1 gene or a protein encoded by the gene and a kit for diagnosing cutaneous pigmentation disease.

Also, it is another object of the present invention to provide a method of providing information necessary for diagnosing cutaneous pigmentation disease, comprising measuring mRNA expression level of the SDF1 gene or expression level of protein encoded by the gene from a patient sample.

In addition, it is another object of the present invention to a screening method for therapeutic agent for cutaneous pigmentation disease or a screening method for skin whitening agent, which comprise measuring mRNA expression level of SDF1 gene or expression level of protein encoded by the gene in the hyperpigmentary cutaneous cells in contact with the test substance.

Furthermore, it is another object of the present invention to a screening method for therapeutic agent for cutaneous pigmentation disease or a screening method for skin whitening agent, which comprise measuring methylation level of a SDF1 promoter region in the hyperpigmentary cutaneous cells in contact with the test substance.

To accomplish the objects of the present disclosure, the present disclosure provides a reagent composition for inhibiting in vitro cutaneous pigmentation comprising stromal cell-derived factor 1 (SDF1), an inducer or activator of SDF1, as an active ingredient.

Also, the present invention provides a pharmaceutical composition for preventing or treating cutaneous pigmentation disease comprising SDF1, an inducer or activator of SDF1, as an active ingredient.

In addition, the present invention provides a cosmetic composition for skin whitening comprising SDF1, an inducer or activator of SDF1, as an active ingredient.

In addition, the present invention provides a functional health food composition for skin whitening comprising SDF1, an inducer or activator of SDF1, as an active ingredient.

In addition, the present invention provides a biomarker composition for diagnosing cutaneous pigmentation disease comprising a SDF1 gene or a protein encoded by the gene.

In addition, the present invention provides a kit for diagnosing cutaneous pigmentation disease comprising a primer or probe specifically binding to the SDF1 gene, an antibody, a peptide, an aptamer, or a compound, which bind specifically to protein encoded by the gene.

In addition, the present invention provides a method of providing information necessary for diagnosing cutaneous pigmentation disease, comprising measuring mRNA expression level of the SDF1 gene or expression level of protein encoded by the gene from a patient sample.

In addition, the present invention provides a screening method for therapeutic agent for cutaneous pigmentation disease, comprising measuring mRNA expression level of SDF1 gene or expression level of protein encoded by the gene in the hyperpigmentary cutaneous cells in contact with the test substance.

In addition, the present invention provides a screening method of therapeutic agent for cutaneous pigmentation disease, comprising measuring methylation level of a SDF1 promoter region in the hyperpigmentary cutaneous cells in contact with the test substance.

In addition, the present invention provides a screening method for skin whitening agent, comprising measuring mRNA expression level of SDF1 gene or expression level of protein encoded by the gene in the hyperpigmentary cutaneous cells in contact with the test substance.

In addition, the present invention provides a screening method for skin whitening agent, comprising measuring methylation level of a SDF1 promoter region in the hyperpigmentary cutaneous cells in contact with the test substance.

DETAILED DESCRIPTION OF THE EMBODIMENTS

Figure 1:
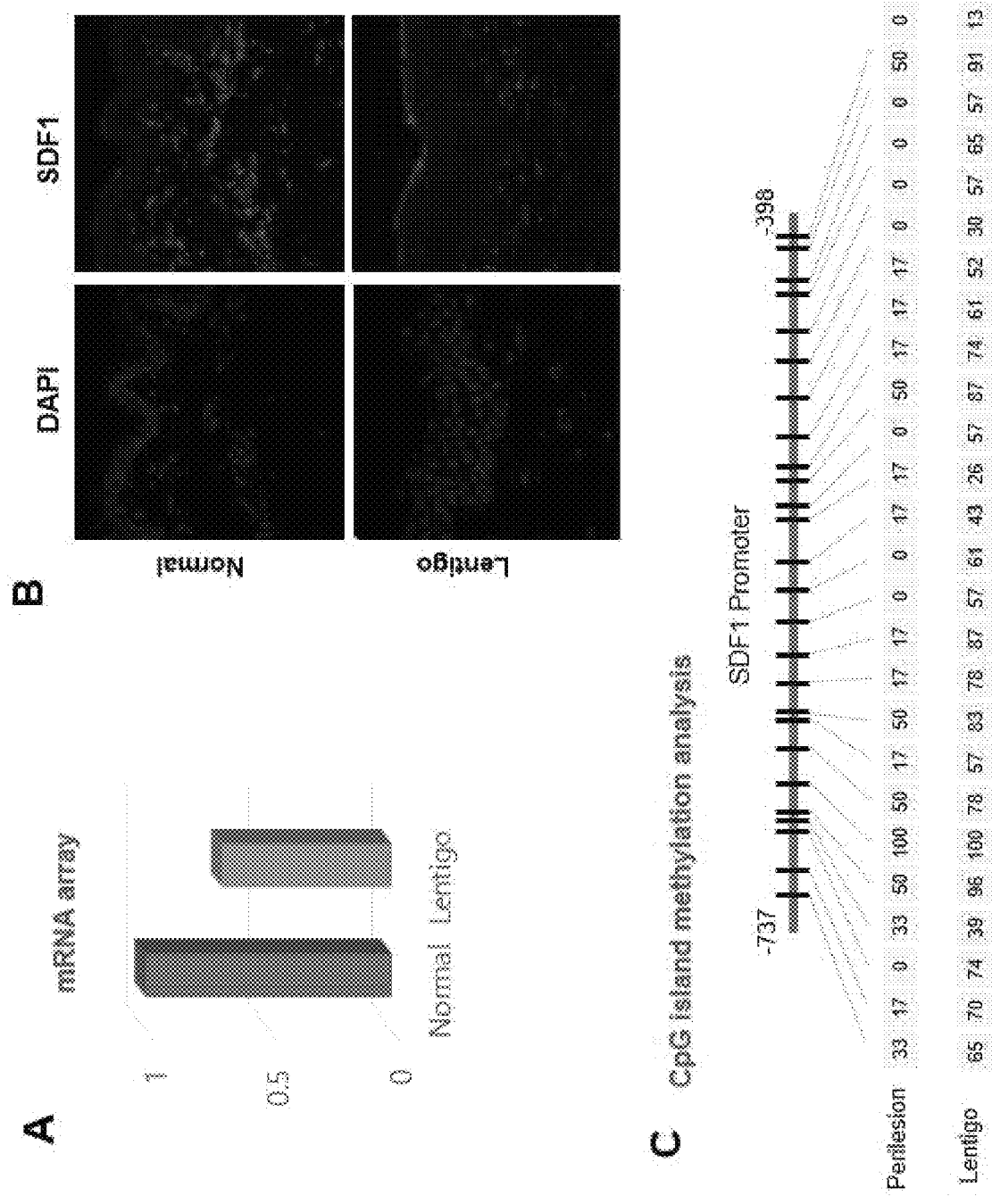
FIG. 1 shows the results of SDF1 expression reduction in hyperpigmentation lesions (lentigo): (A) SDF1 mRNA expression observed by microarray in hyperpigmentation lesions (lentigo) and surrounding normal tissues; (B) SDF1 expression observed by immunohistochemistry in hyperpigmentation lesions (lentigo) and surrounding normal tissues; and (C) degree of methylation of CpG islands in hyperpigmentation lesions tissues.

The present invention provides a reagent composition for inhibiting in vitro cutaneous pigmentation comprising stromal cell-derived factor 1 (SDF1), an inducer or activator of SDF1, as an active ingredient. Preferably, the cutaneous pigment may be melanin, but is not limited thereto.

Specifically, the inducer or activator of SDF1 may be any one selected from the group consisting of a compound, a peptide, an aptamer and an antibody, which bind specifically to SDF1, but it is not limited thereto.

In addition, the present invention provides a pharmaceutical composition for preventing or treating cutaneous pigmentation disease comprising SDF1, an inducer or activator of SDF1, as an active ingredient.

Specially, the cutaneous pigmentation disease is selected from the group consisting of melasma, freckles, lentigo, nevus, pigmentation by drugs, pigmentation after inflammation and hyperpigmentation incurred from dermatitis, but it is not limited thereto.

In addition, the present invention provides a cosmetic composition for skin whitening comprising SDF1, an inducer or activator of SDF1, as an active ingredient.

In addition, the present invention provides a functional health food composition for skin whitening comprising SDF1, an inducer or activator of SDF1, as an active ingredient.

When the composition of the present invention is a pharmaceutical composition, it may further comprise at least one additive selected from the group consisting of carrier, excipient, disintegrant, sweetener, coating agent, swelling agent, lubricants, slip modifiers, flavors, antioxidants, buffers, bacteriostats, diluents, dispersants, surfactants and binders, which are suitable for conventional use in the manufacture of pharmaceutical composition.

Specific examples of carriers, excipients and diluents include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propylhydroxybenzoate, talc, magnesium stearate and mineral oil, and solid formulations for oral administration may include tablets, pills, powders, granules, capsules, etc., and these solid formulations can be prepared by mixing with at least one excipient such as starch, calcium carbonate, sucrose or lactose, gelatin, etc. in the composition. Also, in addition to simple excipients, lubricants such as magnesium stearate and talc may be used. Examples of the liquid formulation for oral administration include suspensions, solutions, emulsions, syrups, etc. and various excipients such as wetting agents, sweeteners, fragrances, preservatives, etc. in addition to water and liquid paraffin which are commonly used as simple diluents. Formulations for parenteral administration include sterilized aqueous solutions, non-aqueous solutions, suspensions, emulsions, freeze-dried formulations, suppositories, and the like. Examples of the non-aqueous solutions or the suspending agent include propylene glycol, polyethylene glycol, vegetable oil such as olive oil, injectable ester such as ethyl oleate, etc. As the suppository base, witepsol, macrogol, tween 61, cacao paper, laurin, glycerogelatin, etc. can be used.

In another embodiment of the present invention, the pharmaceutical composition may be formulated into granules, powders, coated tablets, tablets, pills, capsules, suppositories, gels, syrups, juices, suspensions, emulsions or liquids and then can be used.

According to one embodiment of the present invention, the pharmaceutical composition can be administered via intravenous, intraarterial, intraperitoneal, intramuscular, intrasternal, percutaneous, intranasal, inhalation, topical, rectal, oral, intraocular or intradermal routes to a subject in a conventional manner.

The preferred dosage of the compound varies according to the condition and body weight of the subject, the type and degree of the disease, the drug form, the administration route and the period, and can be appropriately selected by those skilled in the art. According to one embodiment of the present invention, the daily dose may be 0.01 to 200 mg/kg, specifically 0.1 to 200 mg/kg, more particularly 0.1 to 100 mg/kg, though it is not limited thereto. The administration can be administered once a day or divided into several doses, by which the scope of the present invention was not limited.

When the composition of the present invention is a functional health food composition, the health food may further include at least one additive selected from the group consisting of organic acids, phosphates, antioxidants, lactose casein, dextrin, glucose, sugar and sorbitol. The organic acid may be, but is not limited to, citric acid, fumaric acid, adipic acid, lactic acid or malic acid, and the phosphate can be, but are not limited to, sodium phosphate, potassium phosphate, acid pyrophosphate or polyphosphate (polymeric phosphate), and the antioxidant may be, but is not limited to, natural antioxidants such as polyphenols, catechins, alpha-tocopherol, rosemary extract, licorice extract, chitosan, tannic acid or phytic acid, etc.

In another embodiment of the present invention, the functional health food may contain various nutrients, vitamins, minerals (electrolytes), flavoring agents such as synthetic flavors and natural flavors, coloring agents and enhancers (cheese, chocolate, etc.), pectic acid and salts thereof, alginic acid and salts thereof, organic acids, protective colloid thickening agents, pH adjusting agents, stabilizers, preservatives, glycerin, alcohols, carbonating agents used in carbonated drinks and the like. In addition, the food composition according to one embodiment of the present invention may contain flesh for the production of natural fruit juice, fruit juice drink and vegetable drink.

According to one embodiment of the present invention, the formulation of a health food may be in, but is not limited to, the form of solid, powder, granule, tablet, capsule, liquid or drink.

In addition, the functional health food includes, but is not limited to, confectionery, sugars, ice cream products, dairy products, meat products, fish meat products, tofu or glue, edible oils, noodles, teas, beverages, special nutrition foods, health supplements, seasonings, ice, ginseng products, Kimchi pickles, fruits, vegetables, dried products of fruits or vegetables, cut products, fruit juice, vegetable juice, mixed juice thereof, chips, noodles, processed livestock products, processed marine products, processed dairy products, fermented milk products, soybean foods, cereal foods, fermented foods, bakery products, confectionery, meat products, acid drinks, licorice, herbal.

In addition, when the composition of the present invention is a cosmetic composition, the cosmetic composition may be prepared in any formulations conventionally produced in the art, and examples thereof include solutions, suspensions, emulsions, pastes, gels, creams, lotions, powders, soaps, surfactant-containing cleansing, oils, powder foundations, emulsion foundations, wax foundations and sprays, etc., but it is not limited thereto. More specifically, it can be manufactured in the form of a soft lotion, a nutritional lotion, a nutritional cream, a massage cream, an essence, an eye cream, cleansing cream, cleansing foam, cleansing water, a pack, a spray or a powder.

In addition, the present invention provides a biomarker composition for diagnosing cutaneous pigmentation disease comprising a SDF1 gene or a protein encoded by the gene.

The "SDF1 gene or protein encoded by the gene" of the present invention may be NCBI accession no. AY802782, but it is not limited thereto.

The "SDF1" of the present invention may be named as "C-X-C motif chemokine 12 (CXCL12)".

As used herein, the term of "diagnosis" includes determining the susceptibility of an object to a specific disease or disorder, determining whether an object currently has a specific disease or disorder, determining the prognosis of an object having a specific disease or disorder or therametrics (e.g., monitoring the status of an object so as to provide information regarding the therapeutic efficacy).

The present invention also provides a kit for diagnosing cutaneous pigmentation disease comprising a primer or probe specifically binding to the SDF1 gene, an antibody, a peptide, an aptamer, or a compound, which bind specifically to protein encoded by the gene.

In detail, the cutaneous pigmentation disease is selected from the group consisting of melasma, freckles, lentigo, nevus, pigmentation by drugs, pigmentation after inflammation and hyperpigmentary disorders incurred from dermatitis, it is not limited thereto.

As used herein, the term of "primer" refers to a short nucleic acid which has a nucleic acid sequence having a short free 3' hydroxyl group and thus can form base pairs with a complementary template, and serves as a starting point for template strand replication. Primers can initiate DNA synthesis in the presence of reagents for polymerization at appropriate buffer solutions and temperatures (i.e., DNA polymerase or reverse transcriptase) and four different nucleoside triphosphates. The PCR conditions, the lengths of the sense and antisense primers can be appropriately selected according to techniques known in the art.

As used herein, the term of "probe" refers to a nucleic acid fragment such as RNA or DNA, etc. corresponding to a few base or hundreds of bases, which can specifically bind to an mRNA, and because it is labeled, the presence or absence of a specific mRNA and the expression amount can be identified. The probe may be prepared in the form of an oligonucleotide probe, a single strand DNA probe, a double strand DNA probe, or an RNA probe. Selection of suitable probes and hybridization conditions can be appropriately selected according to techniques known in the art.

As used herein, the term of "antibody" which is well known in the art refers a specific immunoglobulin directed against an antigenic site. An antibody in the present invention means an antibody that specifically binds to AWP1 of the present invention and the antibody can be produced according to a conventional method in the art. The form of the antibody includes polyclonal antibody or monoclonal antibody, including all immunoglobulin antibodies. The antibody refers to a complete form having two full-length light chains and two full-length heavy chains. The antibody also includes a special antibody such as a humanized antibody, etc.

In addition, the kit of the present invention includes an antibody specifically binding to a marker component, a secondary antibody conjugate conjugated with a labeling substance of which color is developed upon reaction with a substrate, a coloring substrate solution which undergoes a color reaction with the labeling substance, washing solutions and enzyme reaction stopping solutions, and the like, and may be manufactured as a number of separate packaging or compartments including the reagent components used.

As used herein, the term of "peptide" has a high binding capacity for a target material and does not cause denaturation even during thermal/chemical treatment. Also, because of its small size, it can be used as a fusion protein by attaching to other proteins. It can be used as a diagnostic kit and a drug delivery material because it can be specifically attached to a polymer protein chain.

As used herein, the term of "aptamer" refers to a kind of polynucleotide composed of a specific type of single-stranded nucleic acid (DNA, RNA or modified nucleic acid) having a stable tertiary structure by itself and having the property capable of binding to a target molecule with high affinity and specificity. As described above, since the aptamer is composed of a polynucleotide which is capable of specifically binding to an antigenic substance like an antibody and is more stable than protein, has a simple structure and is easy to synthesize, and thus it can be used in place of an antibody.

In addition, the present invention provides a method of providing information necessary for diagnosing cutaneous pigmentation disease, comprising: (1) measuring mRNA expression level of the SDF1 gene or expression level of protein encoded by the gene from a patient sample; (2) comparing the mRNA expression level of the SDF1 gene or the expression level of the protein encoded by the gene with a control sample; and (3) judging hyperpigmentation when the mRNA expression level of the SDF1 gene or the expression level of the protein encoded by the gene is lower than that of the control sample.

Specifically, when the mRNA expression level of the SDF1 gene or the expression level of the protein encoded by the gene in step of (3) is lower than that of the control sample, methylation in a SDF1 promoter region may be increased. More specifically, the SDF1 promoter region may be a CpG island region of a SDF1 transcription start site (TSS) and the SDF1 promoter region may be represented by SEQ ID NO: 1, but it is not limited thereto.

In detail, the cutaneous pigmentation disease is selected from the group consisting of melasma, freckles, lentigo, nevus, pigmentation by drugs, pigmentation after inflammation and hyperpigmentary disorders incurred from dermatitis, but it is not limited thereto.

In detail, the method for measuring the mRNA expression level may be RT-PCR, competitive RT-PCR, real-time RT-PCR, RNase protection assay (RPA), Northern blotting and DNA chips, but are not limited thereto.

Specifically, the method of measuring the protein expression level may be Western blot, enzyme linked immunosorbent assay (ELISA), radioimmunoassay (RIA), radioimmunodiffusion, Ouchterlony immunodiffusion, rocket immunoelectrophoresis, tissue immunostaining, immunoprecipitation assays, Complement Fixation Assays, FACS and protein chips, but it is not limited thereto.

As used herein, the term of "patient sample" refers to a sample such as a tissue, cell, whole blood, serum, plasma, saliva, sputum, cerebrospinal fluid or urine that have difference from the control group in the expression level of the SDF1 gene or protein as a biomarker for diagnosis of cutaneous pigmentation disease, but it is not limited thereto.

In addition, the present invention provides a screening method for therapeutic agent for cutaneous pigmentation disease, comprising: contacting a test substance with hyperpigmentary cutaneous cells; measuring mRNA expression level of SDF1 gene or expression level of protein encoded by the gene in the hyperpigmentary cutaneous cells in contact with the test substance; and selecting a test substance having increased mRNA expression level of the SDF1 gene or expression level of the protein encoded by the gene as compared with a control sample.

In addition, the present invention provides a screening method of therapeutic agent for cutaneous pigmentation disease, comprising: contacting the test substance with hyperpigmentary cutaneous cells; measuring methylation level of a SDF1 promoter region in the hyperpigmentary cutaneous cells in contact with the test substance; and selecting a test substance having reduced methylation level of the SDF1 promoter region as compared with a control sample.

In detail, the SDF1 promoter region may be a CpG island region of a SDF1 transcription start site (TSS), and the SDF1 promoter region may be represented by SEQ ID NO: 1, but it is not limited thereto.

Specifically, the cutaneous pigmentation disease is selected from the group consisting of melasma, freckles, lentigo, nevus, pigmentation by drugs, pigmentation after inflammation and hyperpigmentary disorders incurred from dermatitis, but it is not limited thereto.

In addition, the present invention provides a screening method for skin whitening agent, comprising: contacting a test substance with hyperpigmentary cutaneous cells; measuring mRNA expression level of SDF1 gene or expression level of protein encoded by the gene in the hyperpigmentary cutaneous cells in contact with the test substance; and selecting a test substance having increased mRNA expression level of the SDF1 gene or expression level of the protein encoded by the gene as compared with a control sample.

In addition, the present invention provides a screening method for skin whitening agent, comprising: contacting the test substance with hyperpigmentary cutaneous cells; measuring methylation level of a SDF1 promoter region in the hyperpigmentary cutaneous cells in contact with the test substance; and selecting a test substance having reduced methylation level of the SDF1 promoter region as compared with a control sample.

In detail, the SDF1 promoter region may be a CpG island region of a SDF1 transcription start site (TSS), and the SDF1 promoter region may be represented by SEQ ID NO: 1, but it is not limited thereto.

The term of "test substance" used in referring to the screening method of the present invention means an unknown candidate substance used in screening to examine whether it affects the expression amount of a gene or affects the expression or activity of a protein. Such sample includes chemicals, nucleotides, antisense-RNA, siRNA (small interference RNA) and natural extracts, but it is not limited thereto.

Hereinafter, the present invention will be described in detail with reference to embodiments that do not limit the present invention. It should be understood that the following embodiments of the present invention are only for embodying the present invention and do not restrict or limit the scope of the present invention. It is therefore to be understood that within the scope of the appended claims, the invention may be practiced otherwise than as specifically described herein.

<Example 1> Reduction of SDF1 Expression in Hyperpigmentation Lesions (Lentigo)

SDF1 expression in hyperpigmentation lesions (lentigo) was decreased comparing with surrounding normal tissues by observing microarray of SDF1 mRNA expression in the hyperpigmentation lesions and the surrounding normal tissues (FIG. 1A).

SDF1 expression was observed by immunohistochemistry in hyperpigmentation lesions (lentigo) and surrounding normal tissues. SDF1 (R&D, cat no. MAB350) was used as an antibody. As a result, it was confirmed that expression of SDF1 was reduced in the hyperpigmentation lesion portion than the surrounding normal tissue (FIG. 1B).

SDF1 is also known as C-X-C motif chemokine 12 (CXCL12), and the CXCL12 promoter of the CXCL family has CpG islands. As a result of the methylation analysis screening, it was observed that CpG island methylation of the transcription start site (TSS) portion was increased (FIG. 1C).

Genomic DNA was isolated from surrounding normal tissues and hyperpigmentation lesions and then modified through Bisulfite kit (Quiazen, Cat. 59824) and forward 5'-GTTTTTTATTGGTTTTT ATTTAGTTTT-3', reverse 5'-TACCTCCACCCCCACTATAT-3' were used as a bisulfite sequencing primer. From the sequence analysis data, the degree of methylation of the promoter region of SDF1 obtained through the primers was compared with the surrounding normal tissues. As a result, it was observed that methylation of CpG islands was increased in hyperpigmentation lesion tissues (FIG. 1C).

<Example 2> Confirmation of SDF1 and CXCR4 Expression in Skin

Experiments were performed to examine the expression levels of SDF1 and CXCR4 in the skin.

Figure 2:
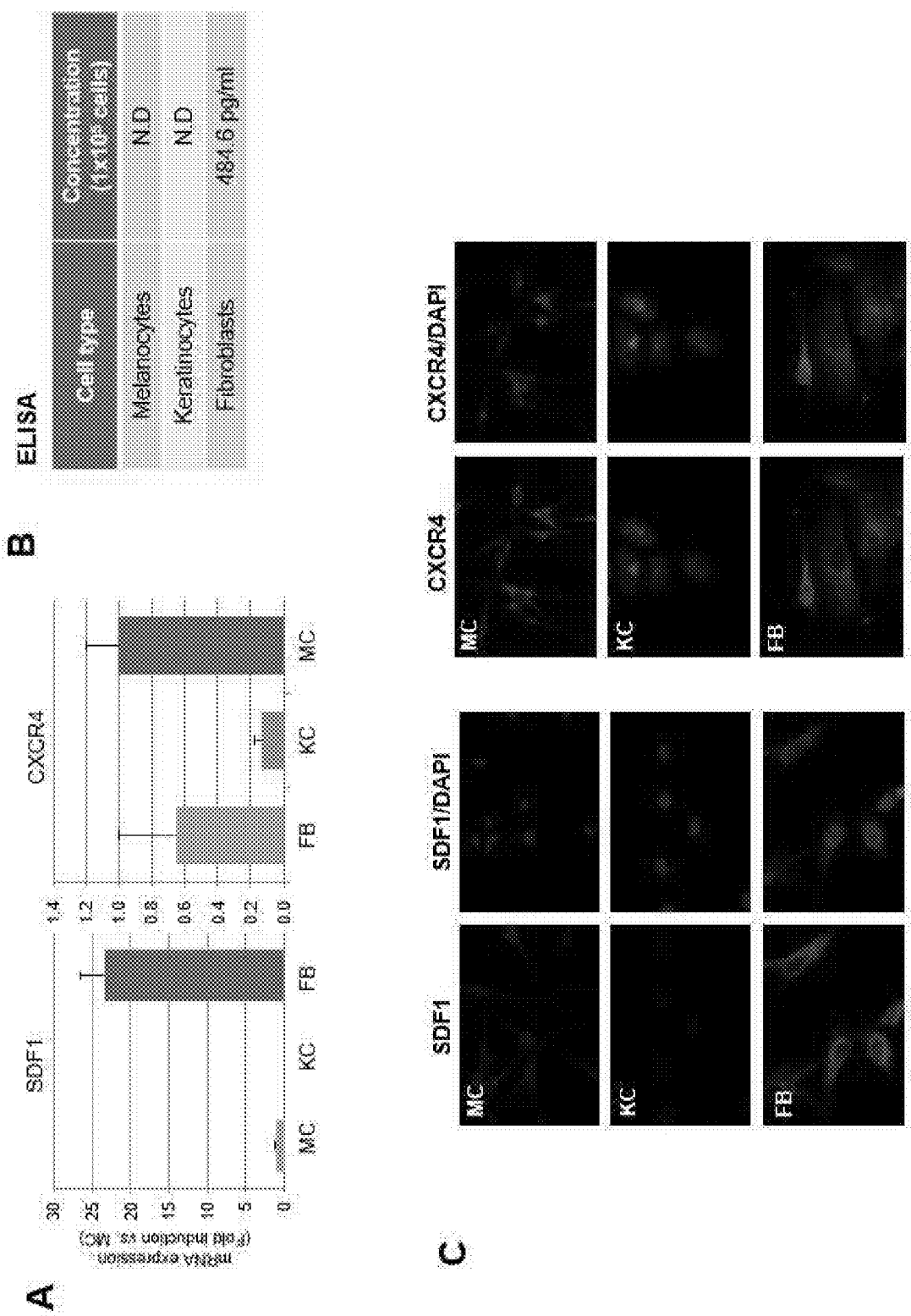
FIG. 2 shows the results of experiments for expression levels of SDF1 and CXCR4 in the skin: (A) expression level observed by real time PCR; (B) SDF1 secretion in fibroblasts through ELISA; and (C) protein expression level observed by immunohistochemical analysis.

The expression level was observed by real time PCR. As the primers, SDF1 (forward 5'-TGC CAG AGC CAA CGT CA-3', reverse 5'-CAG CCG GGC TAC AAT CTG AA-3') and CXCR4 (forward 5'-CAT CAG TCT GGA CCG CTA CC-3', reverse 5'-GGA TCC AGA CGC CAA CAT AG-3')

were used. As a result, it was observed that SDF1 was expressed in a large amount in fibroblast, and CXCR4 was observed to be expressed in fibroblasts and melanocytes (FIG. 2A).

In addition, SDF1 secretion was confirmed by ELISA in fibroblasts. Protein levels were measured by ELISA in the supernatant in which each cell was cultured, and a large amount of SDF1 was observed to be secreted in fibroblasts (FIG. 2B).

On the other hand, SDF1 in a large amount was expressed in fibroblasts and CXCR4 in a large amount was expressed in melanocytes and fibroblasts (FIG. 2C), as a result of confirming protein expression levels by immunohistochemical analysis.

<Example 3> SDF1 Reducing Pigmentation in Human Melanocytes

In order to confirm the effect of SDF1 on melanogenesis, a lentivirus in which SDF1 gene was inserted into fibroblasts and a control lentivirus were infected with each other and co-cultured with melanocytes, and then changes in pigmentation in melanocytes was observed.

Figure 3:
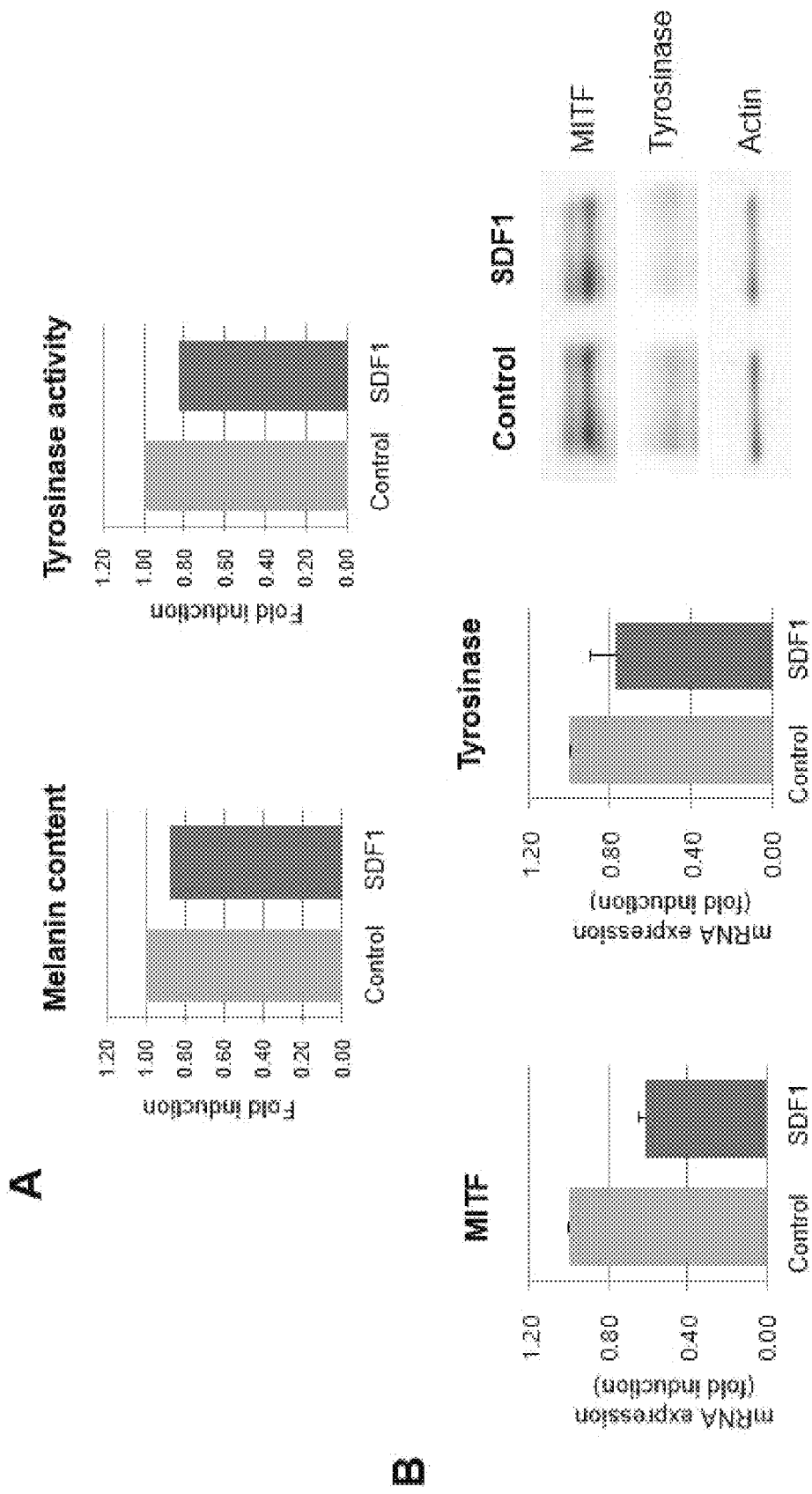
FIG. 3 shows the results for SDF1 reducing pigmentation in human melanocytes: (A) the result of confirming that overexpression of SDF1 inhibits pigmentation by analysis of melanin content and tyrosinase activity; and (B) the result of confirming that SDF1 inhibits expression of RNA and protein by real-time PCR and western blot analysis of MITF and tyrosinase expression.

The melanin content and tyrosinase activity of melanocytes were observed when the fibroblasts infected with the control lentivirus and SDF1 lentivirus were co-cultured with melanocytes which are cells producing melanin. As a result, it was confirmed that the melanin content in the melanocytes co-cultured with fibroblasts infected with SDF1 lentivirus was significantly lower than that in the control group, and the tyrosinase activity was also significantly decreased in the melanocytes treated with SDF1-overexpressed fibroblasts (FIG. 3A).

In addition, when the control virus vector and the SDF1-infected fibroblast were co-cultured with melanocyte which is a melanocyte-producing cells, mRNA levels of MITF (Forward 5'-AGA ACA GCA ACG CGC AAA AGA AC-3', Reverse 5'-TGA TGA TCC GAT TCA CCA AAT CTG-3') and tyrosinase (Forward 5'-CAC CAC TTG GGC CTC AAT TTC-3', Reverse 5'-AAA GCC AAA CTT GCA GTT TCC AC-3') were observed by real-time PCR. As a result, when the SDF1-overexpressed fibroblasts were co-cultured with melanocytes, mRNA expression of MITF and tyrosinase was effectively inhibited, and the protein levels of MITF and tyrosinase were observed by western blotting and significant results were also obtained (FIG. 3B).

<Example 4> Confirmation of Increased Melanogenesis by Down-Regulation of SDF1 in Human Melanocytes When the expression of SDF1 was inhibited in fibroblasts, cells which were infected with lentivirus of shSDF1 and lentivirus of shControl as the control group were co-cultured with melanocytes to confirm the effect on melanogenesis. SDF1 (1) (3'-TATTTTGAGATGCTTGACGTTG, 5'-AAACGTCAAGCATCTCAAAATA) and SDF1 (2) (3'-TGTGTTGAGAATTTTGAGATGC, 5'-ACATCT-CAAAATTCTCAACACA) were used as shSDF1.

Figure 4:
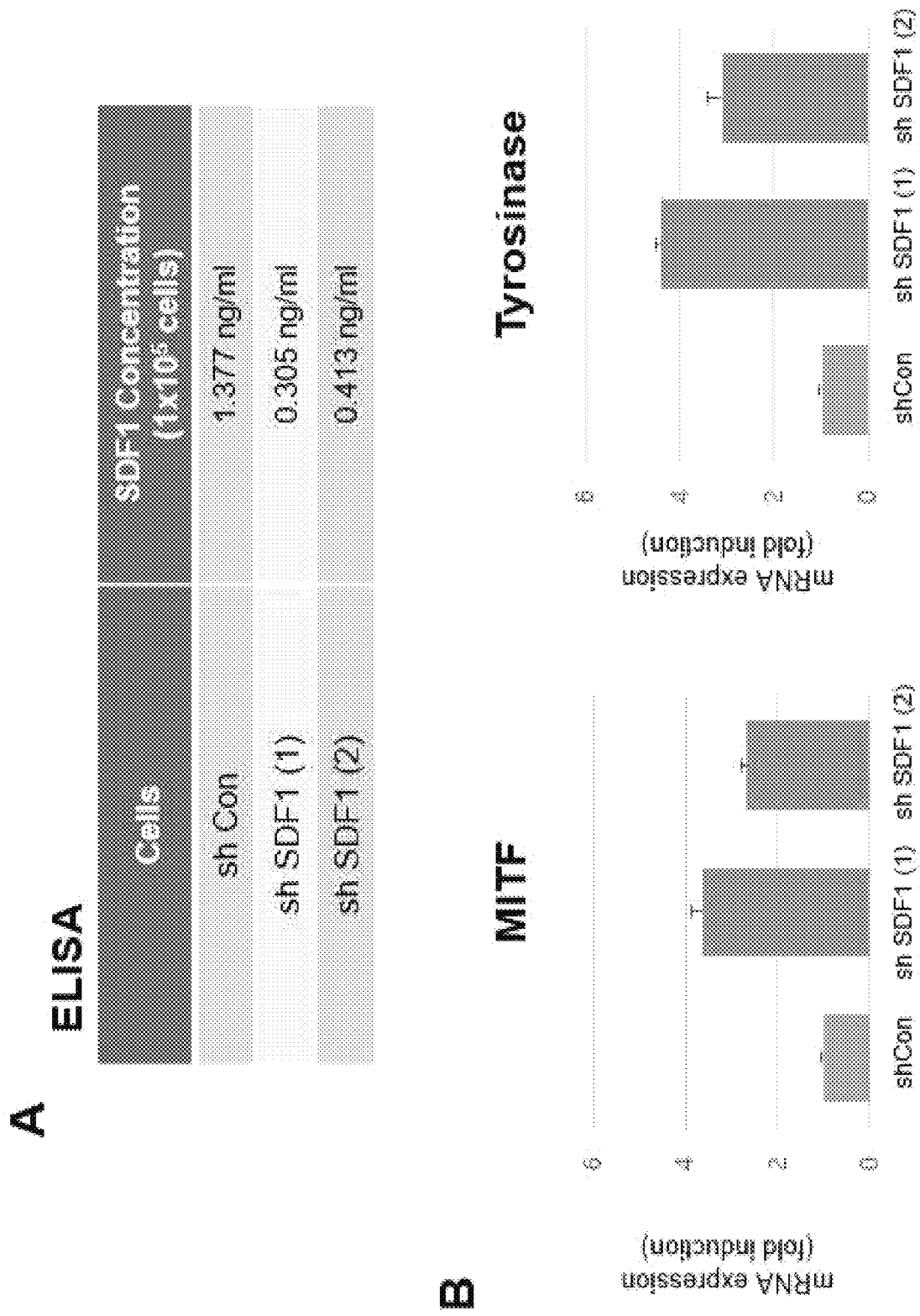
FIG. 4 shows the results of confirming the increase of melanin production by down-regulation of SDF1 in human melanocytes: (A) SDF1 protein level observed by ELISA in the supernatant of cells infected with shControl lentivirus and each shSDF1 lentivirus; and (B) levels of MITF and tyrosinase observed by real-time PCR after co-culturing fibroblasts infected with hControl lentivirus and each shSDF1 lentivirus with melanocytes.

SDF1 protein levels were observed in the supernatant of cells infected with shControl lentivirus and each shSDF1 lentivirus by ELISA (FIG. 4A).

In addition, the fibroblasts infected with the shControl lentivirus and each shSDF1 lentivirus, were co-cultured with melanocytes, and the levels of MITF and tyrosinase were observed by real-time PCR. As a result, it was observed that the levels of MITF and tyrosinase were significantly increased in melanocytes when fibroblast infected with shSDF1 lentivirus was co-cultured (FIG. 4B).

Example 5: Recombinant Human SDF1 Reducing Melanin Synthesis in Ex Vivo Skin Culture Experiments were performed to observe the effect of SDF1 on skin pigmentation.

Figure 5:
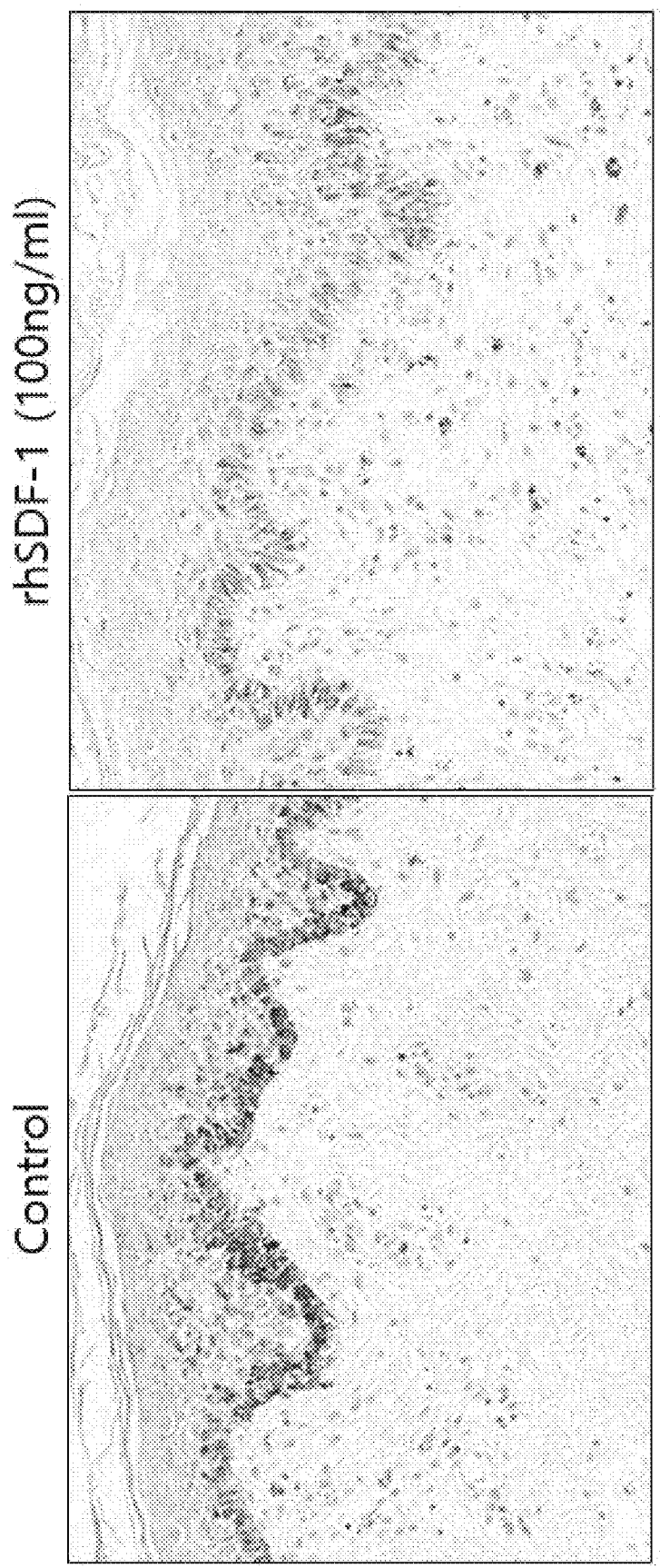
FIG. 5 shows the results for recombinant human SDF1 reducing melanin synthesis in ex vivo skin cultures.

Ex vivo human skin was cultured for 3 days each with or without the treatment of recombinant human SDF1 (rhSDF1, 100 ng/ml). After incubation, the cells were reacted in 10% formalin solution at 42° C. overnight. Fontana-Masson staining was performed after fixing the skin. A remarkable decrease in pigmentation was observed in the skin cultured with rhSDF1 (FIG. 5).

In conclusion, SDF-1 expression was decreased in senile hyperpigmentation lesion (lentigo) and expression of SDF-1 in skin cells was observed was found to be prominent in fibroblasts, and expression of CXCR4, a receptor, was confirmed to be marked in melanocytes. In addition, SDF-1 secreted from fibroblasts was confirmed to inhibit the melanin synthesis of melanocytes and the promotion of melanogenesis of melanocytes by inhibiting SDF-1 expression from fibroblasts was confirmed. Finally, it was confirmed that melanin synthesis was reduced by directly treating skin with SDF-1 recombinant protein.

INDUSTRIAL APPLICABILITY

The present invention relates to a composition for regulating cutaneous pigmentation or a composition for skin whitening comprising stromal cell-derived factor 1 (SDF1), as an active ingredient and the role of SDF1 in the regulation of cutaneous pigmentation was investigated. The present inventors confirmed a decrease in SDF1 expression in senile hyperpigmentation lesion (lentigo). In addition, it was confirmed that SDF1 secreted from fibroblasts inhibits melanogenesis of melanocytes and inhibition of expression of fibroblast-derived SDF1 promotes melanogenesis of melanocytes. Therefore, SDF1 is expected to be an effective treatment strategy for cutaneous pigmentation diseases such as hyperpigmentation.

What is claimed is:

1. A method of treating cutaneous pigmentation disease in a subject in need thereof, comprising: providing a pharmaceutical composition consisting of SDF1 and a carrier and administering the pharmaceutical composition to a skin of the subject, wherein the cutaneous pigmentation is treated, wherein the cutaneous pigmentation disease is selected from the group consisting of melasma, freckles, lentigo, nevus, pigmentation by drugs, pigmentation after inflammation and hyperpigmentation incurred from dermatitis.

2. A skin whitening method, comprising: providing a pharmaceutical composition consisting of SDF1 and a carrier and administering the pharmaceutical composition to a skin of a subject, wherein the skin of subject becomes whitened.

* * * * *